(12) United States Patent
Cho et al.

(10) Patent No.: US 7,338,808 B2
(45) Date of Patent: Mar. 4, 2008

(54) METHOD AND APPARATUS FOR DETERMINING ZETA POTENTIAL USING ALTERNATING CURRENT ELECTRIC FIELD AND T CHANNEL

(75) Inventors: Yoon-kyoung Cho, Kyungki-do (KR); Sang-min Shin, Gyeongsangbuk-do (KR); In-seok Kang, Gyeongsangbuk-do (KR); Geun-bae Lim, Kyungki-do (KR)

(73) Assignee: Samsung Electronics Co., Ltd. (KR)

( * ) Notice: Subject to any disclaimer, the term of this patent is extended or adjusted under 35 U.S.C. 154(b) by 746 days.

(21) Appl. No.: 10/698,507

(22) Filed: Oct. 31, 2003

(65) Prior Publication Data

US 2004/0140210 A1      Jul. 22, 2004

(30) Foreign Application Priority Data

Jan. 21, 2003     (KR) ...................... 10-2003-0004108

(51) Int. Cl.
  *G01N 25/18*   (2006.01)
  *G01N 27/00*   (2006.01)
  *B01L 3/02*    (2006.01)
  *B32B 5/02*    (2006.01)
  *B32B 27/04*   (2006.01)

(52) U.S. Cl. ...................... 436/149; 422/81; 422/82.01; 422/50; 422/68.1; 422/82.02; 436/43; 436/63; 73/1.01; 73/1.02; 73/53.01; 204/164; 204/450; 204/452; 204/457; 204/458; 204/461; 204/193; 204/194; 204/400

(58) Field of Classification Search ................. 73/1.01, 73/1.02, 53.01; 422/50, 68.1, 81, 82.01, 422/82.02; 436/43, 63, 149; 204/164, 450, 204/452, 457, 458, 461, 193, 194, 400; 702/1, 702/57, 65

See application file for complete search history.

(56) References Cited

U.S. PATENT DOCUMENTS 3,454,487 A  7/1969  Riddick ...................... 204/299
4,602,989 A  7/1986  Culkin ...................... 204/180.1
6,051,124 A  4/2000  Aoki .......................... 204/600

FOREIGN PATENT DOCUMENTS

GB      2 368 904 A      5/2002

OTHER PUBLICATIONS

"Determination of the Zeta Potential and the Surface Conductivity by Streaming Potential and Streaming Current Measurements" Authors: Ralph Zimmermann, Wolfgang Jenschke, Heinz Korber, Carsten Werner; Technisches Messen TM, R. Oldenbourg Verlag. Munchen, DE, vol. 67, No. 9, Sep. 2000, pp. 353-360, XP001132480, ISSN: 0171-8096.

(Continued)

*Primary Examiner*—Brian Sines
(74) *Attorney, Agent, or Firm*—Cantor Colburn LLP (57) ABSTRACT

Provided is a method for determining a zeta potential generated between a solid wall and a solution. The method includes (a) injecting an electrolyte solution into a first inlet of a T channel, which is provided with first and second inlet electrodes and a grounded outlet electrode, and a mixed solution of the electrolyte solution and a fluorescent dye into a second channel of the T channel and maintaining a steady-state of the two solutions; (b) applying a direct current electric field from the first and second electrodes to the outlet electrode to form an interface between the electrolyte solution and the mixed solution; (c) applying an alternating current electric field from one of the two inlet electrodes to the outlet electrode to oscillate the interface; and (d) measuring an amplitude of oscillation of the interface and determining the zeta potential from the standard relationship between the zeta potential and the amplitude.

4 Claims, 7 Drawing Sheets

OTHER PUBLICATIONS

European Search Report of EP 03 02 6144; Date of Completion of the Search: Dec. 15, 2004.
"The ζ-Potential of Glass Surface in Contact with Aqueous Solutions"; Authors: Yongan Gu and Dongqing Li; Academic Press; Journal of Colloid and Interface Science, vol. 226; 2000; pp. 328-339.
"Current-Monitoring Method for Measuring the Electroosmotic Flow Rate in Capillary Zone Electrophoresis"; Authors: Xiaohua Huang, Manuel J. Gordon and Richard N. Zare; American Chemical Society; Anal. Chem., vol. 60; 1988; pp. 1837-1838.

METHOD AND APPARATUS FOR DETERMINING ZETA POTENTIAL USING ALTERNATING CURRENT ELECTRIC FIELD AND T CHANNEL

BACKGROUND OF THE INVENTION

This application claims the priority of Korean Patent Application No. 2003-4108, filed on Jan. 21, 2003, in the Korean Intellectual Property Office, the disclosure of which is incorporated herein in its entirety by reference.

1. Field of the Invention

The present invention relates to a method and apparatus for determining a zeta potential generated between a channel wall and a solution.

2. Description of the Related Art

When a glass microchannel or capillary is filled with an electrolyte solution, an electric double layer is formed at an interface between a liquid phase and a solid phase. If an electric field is applied tangentially to the electric double layer, an electric body force is exerted on the excess counter ions in the electric double layer, and thus an electroosmotic flow is generated. The electroosmotic flow is used as an important driving force in miniaturized analysis chips such as Lab-On-a-Chip (LOC). For the case where there is no pressure gradient between both ends of a channel, the Debye-Huckel theory is applied, and the electric double layer is much less than the characteristic length scale of the channel, the rate of the electroosmotic flow (u) is represented by Helmholtz-Smoluchowski equation as Equation 1:

$$u = -(\in \zeta E)/\mu, \quad \text{Equation 1;}$$

where $\in$ is the dielectric constant of an electrolyte solution, $\zeta$ is the zeta potential at the electrolyte solution and the channel, $\mu$ is the viscosity of the electrolyte solution, and E is the electric field. The dielectric constant and viscosity of the electrolyte solution, which are physical property values of the electrolyte solution, are given as constant values with respect to the electric field. In this regard, provided that the zeta potential is determined, the rate of the electroosmotic flow in a channel can be obtained from a linear relationship between the rate of the electroosmotic flow and the external electric field. The rate of the electroosmotic flow serves as the most basic data for fluid control such as fluid separation and migration on the LOC.

Conventionally, the zeta potential of protein particles or particles dispersed in the dispersion system is mainly determined by measuring the mobility of particles. However, in order for the electroosmotic flow to be widely used as a driving force in miniaturized analysis chips, determination of the zeta potential generated between an electrolyte solution and a channel wall is required, rather than the determination of the zeta potential of particles. Methods of determining the zeta potential at a solid-solution interface are known in the art.

For example, U.S. Pat. No. 6,051,124 discloses a method of determining a zeta potential using a reflected laser beam. However, there is no mention to a solid.

Also, a particle tracking method is widely used in conventional fluid flow experiments. As a result of observation of tracer particles seeded in a fluid for a predetermined time, a straight particle trajectory is visualized. Since the displacement of the tracer particles for a predetermined time is given, the flow rate can be calculated. Therefore, a zeta potential can be determined by using Equation 1. However, tracer particles must be seeded to some degree in a zeta potential determining channel to ensure the zeta potential determination. Also, in a case where the tracer particles are electrically charged, an electrophoretic mobility due to the charged particles must be considered. In addition, since the wall surface of the previously used channel may be contaminated by the tracer particles, it is difficult to reuse the channel for additional experiments.

A zeta potential can also be determined by a current monitoring method based on the following principle [Anal. Chem. 1988, 60, 1837-1838]. When a capillary channel is filled with electrolytes with different concentrations and a voltage is applied to both ends of the channel, an electric current decreases or increases due to a change of the electrolyte concentration with time. When the distance between both ends of the channel is given and the time elapsed until there is no current change is measured, the rate of the electroosmotic flow can be calculated. Therefore, the zeta potential can be determined according to Equation 1. Due to simple experiment equipments, this method has widely been used for determining the zeta potential.

Determination of a zeta potential by a stream potential method is based on the following principle [Journal of Colloid and Interface Science 226, 328-339, 2000]. When a pressure gradient is induced at both ends of an electroosmotic determining channel, ions of an electric double layer on the wall of the channel are displaced, thereby causing an electric potential difference between both ends of the channel. When a steady-state is reached, a constant electric potential is maintained. This electric potential difference is called streaming potential. In order to determine the zeta potential using the streaming potential, data such as electroconductivity and pressure difference are required. In particular, regression analysis using multiple data set obtained by varying the length of the channel is required. For this reason, such a streaming potential method is relatively accurate, unlike the particle tracking method and current monitoring method. However, as mentioned above, because multiple data set for the regression analysis must be determined by previous experiments, the streaming potential method is not suitable for rapid measurement. Also, more experiment equipments to be attached to both ends of the channel are required, when compared to the above-described two methods.

SUMMARY OF THE INVENTION

The present invention provides a method of determining a zeta potential without using tracer particles.

The present invention also provides an apparatus for determining a zeta potential generated between a solid wall and a solution without using tracer particles.

According to an aspect of the present invention, there is provided a method for determining a zeta potential generated between a channel wall and a fluid, the method comprising: (a) injecting an electrolyte solution into a first inlet of a T channel, which is provided with first and second inlet electrodes and a grounded outlet electrode, and a mixed solution of the electrolyte solution and a fluorescent dye into a second channel of the T channel and maintaining a steady-state of the two solutions; (b) applying a direct current electric field from the first and second electrodes to the outlet electrode to form an interface between the electrolyte solution and the mixed solution; (c) applying an alternating current electric field from one of the two inlet electrodes to the outlet electrode to oscillate the interface; and (d) measuring an amplitude of oscillation of the interface and determining the zeta potential from the standard relationship between the zeta potential and the amplitude.

According to another aspect of the present invention, there is provided an apparatus for determining a zeta potential generated between a channel wall and a fluid, the apparatus comprising: (a) a T channel comprising first and second inlets and an outlet; (b) first and second inlet electrodes and an outlet electrode, which are installed at the first and second inlets, and the outlet, respectively; (c) electric field application means for applying an electric field between the first inlet electrode and the outlet electrode and between the second inlet electrode and the outlet electrode; (d) two reservoirs, one of which is connected to the first inlet to feed an electrolyte solution and the other is connected to the second inlet to feed a mixed solution of the electrolyte solution and a fluorescent dye; and (e) means for measuring an amplitude of oscillation of an interface between the electrolyte solution and the mixed solution.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

In a zeta potential determining method according to the present invention, the amplitude of oscillation of an interface between a T channel and a solution can be measured by a fluorescence microscope, for example. A direct current (DC) electric field may vary depending on the length and physical properties of the channel but preferably ranges from 100 to 2,000 V/cm. The magnitude ($\in$) of the alternating current (AC) electric field, which is applied from one of two inlet electrodes to a grounded outlet electrode, may vary depending on the width of the channel. Although a larger amplitude is preferable for an easy amplitude measurement, the amplitude measurement is impossible in a case where the amplitude exceeds the width of the channel. When the widths of an inlet, an outlet, and a channel portion are the same, about 100 μm, the AC electric field magnitude ($\in$) of 0.3 dl or less is preferable, but is not limited thereto. The frequency (f) of an AC electric field can be appropriately adjusted according to an image measuring speed of an amplitude measuring device, for example a CCD camera. Preferably, the frequency (f) is in the range of 1 to 10 Hz. The channel used in the present invention comprises two inlets and an outlet. The size and the shape of the channel are not particularly limited and may vary depending on the channel wall for amplitude measurement and the electrolyte solution. For example, the channel may be of a rectangular pillar form with a width of 1 to 1,000 μm and a height of 1 to 5,000 μm. The wall of the channel may be made of quartz, glass, Si, $SiO_2$, PDMS, and PMMA. In addition, a plastic material may be used. The flow rate of the electrolyte solution and the mixed solution may vary depending on the applied AC electric field and the zeta potential, but preferably ranges from 100 to 1,000 μm/sec. The electrolyte solution may be a conventional electrolyte solution such as a NaCl solution. The fluorescent dye may also be a conventional fluorescent dye such as rhodamine and FITC.

Preferably, the amplitude measuring means is a fluorescence microscope.

Figure 1:
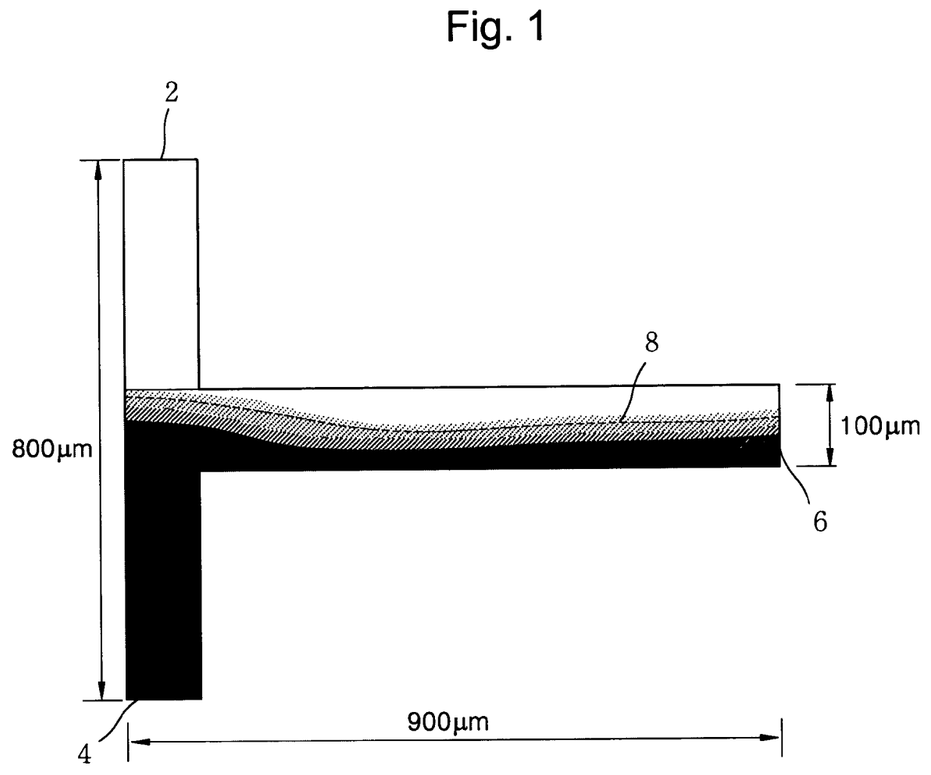
FIG. 1 is a view of an example of a waveform at an interface between two solutions in a T channel, according to the present invention.

Hereinafter, the present invention will be described in more detail with reference to FIG. 1 showing an example of a waveform at the interface between the T channel and the solution, but is not limited thereto.

First, an electrolyte solution is injected into one of two inlets 2 and 4 (for example, the inlet 4) and a mixed solution of a fluorescent dye and the electrolyte solution is injected into the other inlet (for example, the inlet 2). The injected electrolyte solution and mixed solution flow toward an outlet 6 through a channel portion in which the two solutions are merged (simply referred to as "merged channel", hereinafter). The flow of the two solutions continues until a steady-state corresponding to no pressure gradient over the entire section of the channel is reached. When a steady-state of the two solutions is reached, the same DC voltage ($V_0$) is applied from the two inlets to the outlet. At this time, an interface between the two solutions appears in the merged channel. Also, because the rate of an electroosmotic flow is very low and the size of the channel is very small, the solutions flow at a very low Reynolds number. As a result, the fluid property corresponds to the region where the Stokes number is about zero. The interface in the merged channel is very distinct and has very small width, although there is more or less according to the diffusion coefficient of the electrolyte solution. Therefore, it is very easy to measure the amplitude of oscillation of the interface.

Next, in order to oscillate the interface, an AC voltage with a constant $\in$ and f, is applied from one inlet 2 to the outlet. Here, $\in$ indicates the magnitude of an AC voltage and is in the range of 0 to 1 and f indicates the frequency of an AC voltage. The waveform at the interface between the two solutions has a close relationship with $\in$ and f. In this case, the voltage of the channel portion to which an AC voltage is applied is expressed as $V=V_0(1+\in\sin(360\,ft))$. Referring to FIG. 1, the interface 8 between the two solutions appears distinctly. The channel used in FIG. 1 is a rectangular pillar-shaped channel with a width of 100 μm and a height of 50 μm, and $\in$ and f is 0.3 and 1 Hz, respectively.

Hereinafter, the present invention will be described more specifically by examples. However, the following examples are provided only for illustrations and thus the present invention is not limited to or by them.

EXAMPLE

Simulation was performed using a T channel with a size and a shape as shown in FIG. 1.

Example 1

In this simulation, there was used a rectangular pillar-shaped T channel with the total length of first and second inlet channels of 800 μm, the length of a merged channel of 900 μm, the width of each channel of 100 μm, and the height of each channel of 50 μm. An outlet of the merged channel was grounded.

Figure 2A:
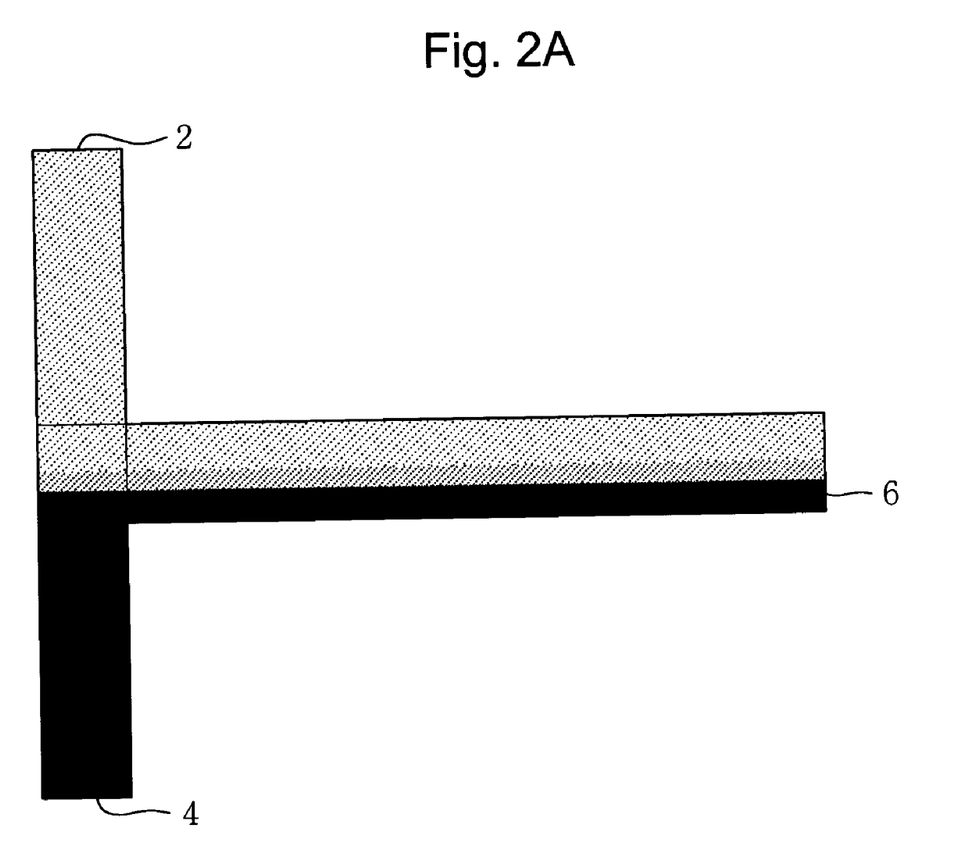
FIGS. 2A through 2C are views of waveforms at the interface which changes according to an alternating current electric field application duration.
Figure 2B:
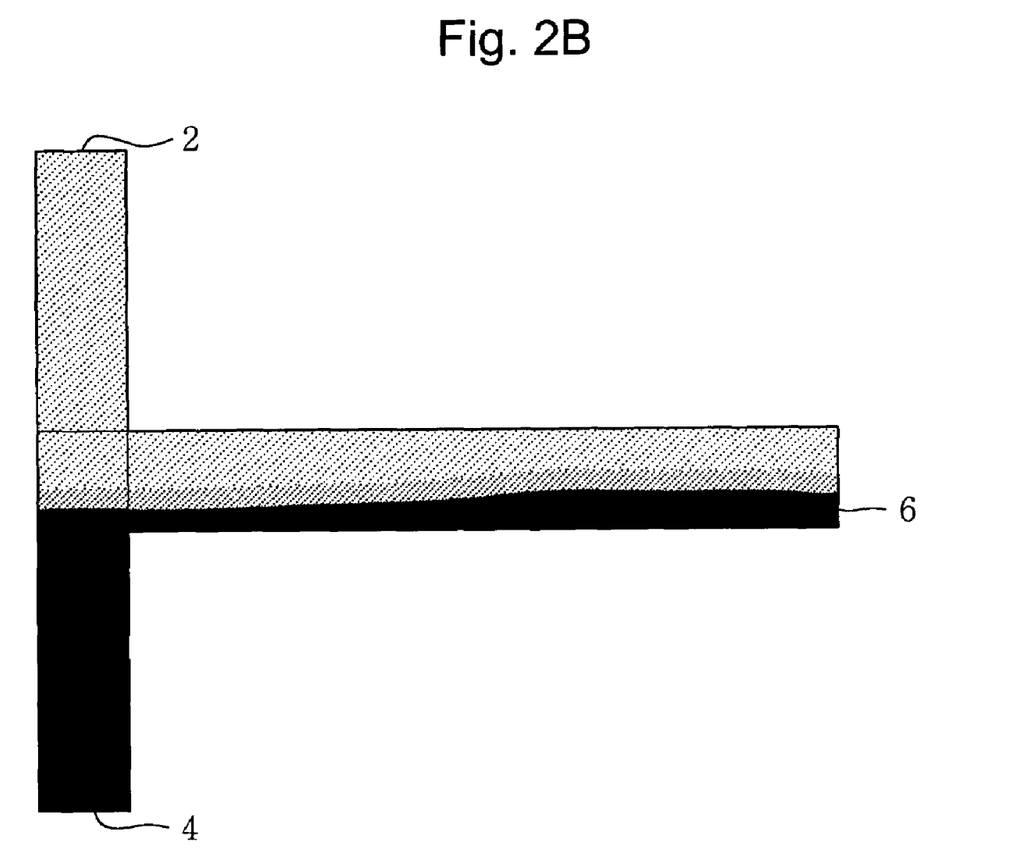
Figure 2C:
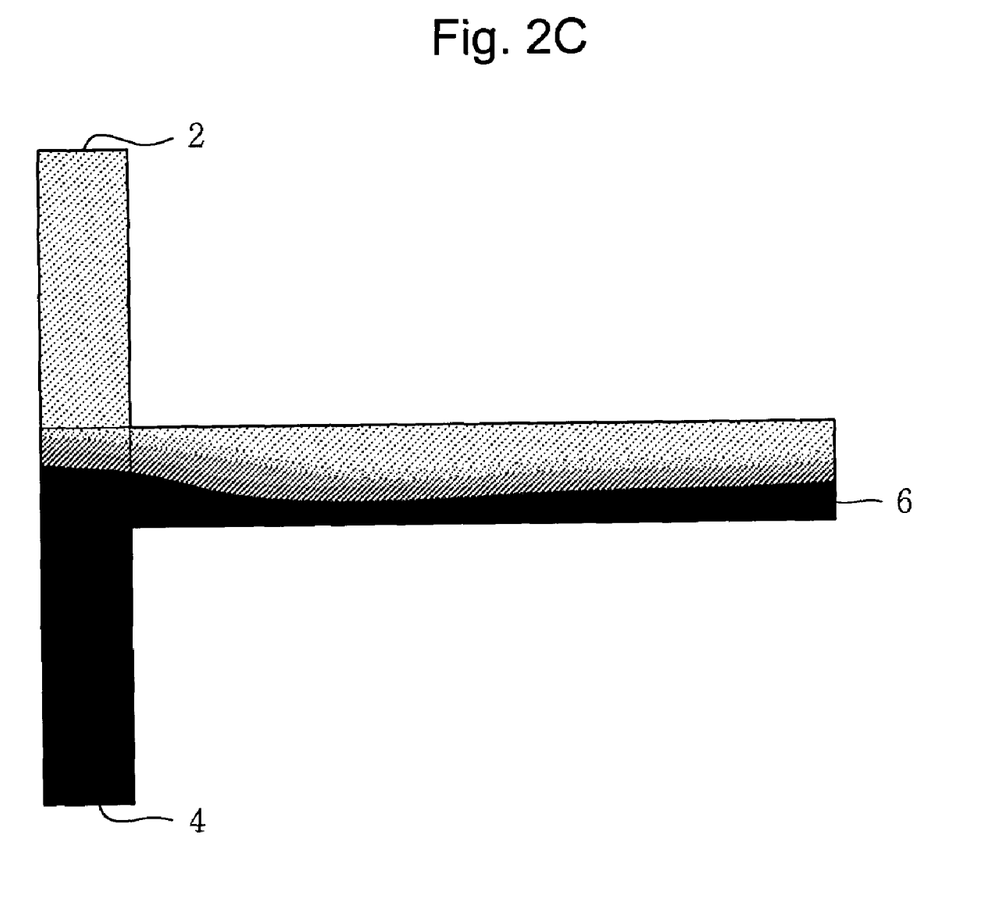
Figure 3:
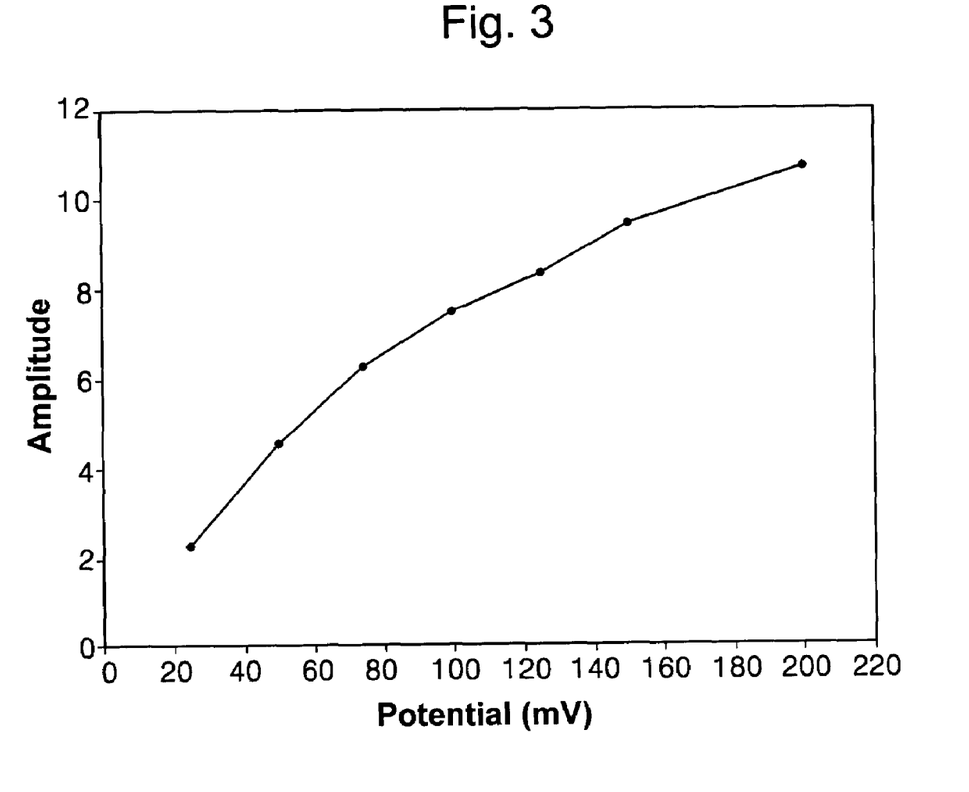
FIG. 3 is a graph showing the relationship between the zeta potential of a channel wall and the amplitude of oscillation of the interface.

The simulation results are shown in FIGS. 1 through 3. FIG. 1 is a view of an example of a waveform at an interface that appears after application of an AC voltage. As shown in FIG. 1, the interface 8 was distinctly observed. FIGS. 2A through 2C are views of waveforms at the interface that changes according to an AC voltage application duration. In this case, a DC voltage of $V_0$ was applied to the first inlet 2 and a DC and VC combined voltage of $V=V_0(1+0.3 \sin(360\, t))$ was applied to the second inlet 4. The zeta potential was −50 mV and the time elapsed after application of an AC voltage was 7.0, 7.5, and 8.0 seconds, respectively. FIG. 3 is a graph showing an example of the standard relationship between the zeta potential and the amplitude of oscillation of the interface. In order to examine the standard relationship, the amplitude was measured with varying the zeta potential of the channel wall using the CFD-simulation. In this case, the largest amplitude at one cycle was selected. The CFD simulation was performed using a commercially available simulation program, CFD-ACE+(CFD Research Corporation, USA). The flow rate was 632 μm/sec, an electrolyte solution was a 1M NaCl solution, and a fluorescent dye was rhodamine.

As seen from FIG. 3, there exists a nearly linear relationship between the amplitude and the zeta potential. Therefore, the zeta potential can be determined by measuring the amplitude.

Example 2

The relationship between the oscillating amplitude and the zeta potential was numerically investigated in Example 1. In this example, an experiment was performed to check the accuracy of the simulation results of Example 1.

The T channel had the same dimensions with the channel used in Example 1 except that the outlet channel had a length of 0.7 cm and the two inlet channels had a length of 1 cm. The magnitude of $V_0$ was 600V and $\in$ was 0.5, i.e., $V=600(1+0.5 \sin(360\, t))$. The amplitude of merged layer oscillating at the channel junction depends on the frequency of applied electric field.

NaCl solution in the concentration of 1 mM and 10 mM was used. The zeta potential in the two cases was measured using a commercially available zeta potential measuring device, ELS-8000 (OTSUKA Electronics, Japan). This piece of equipment (OTSUKA Electronics, Japan) determines the zeta potential using the stream potential method (*Journal of Colloid and Interface Science* 226, 328-339, 2000). The measured zeta potential of the 1 mM and 10 mM NaCl solution was −53.9 mV and −34.9 mV, respectively.

This experiment demonstrates qualitatively that the zeta potential of the 1 mM and 10 mM NaCl solution can be also determined by the present method as explained below.

Figure 4A:
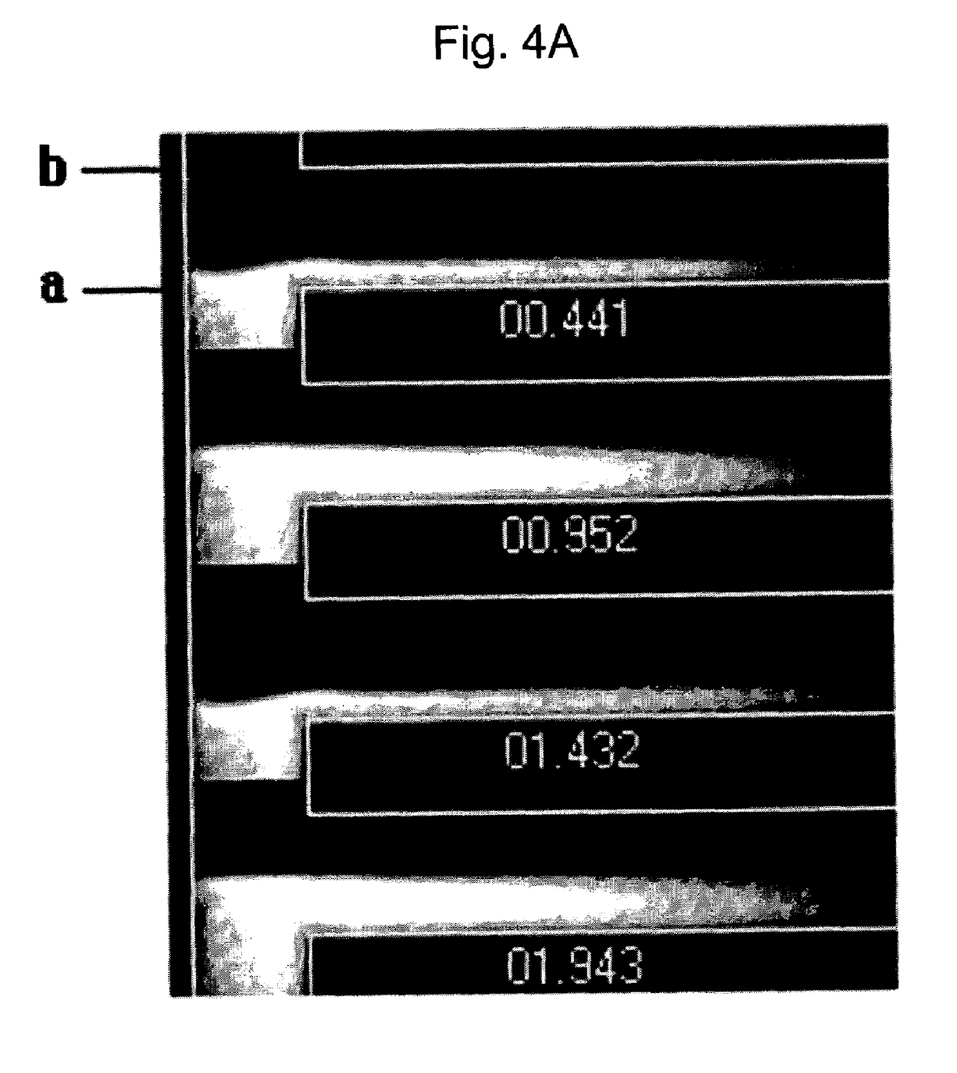
FIG. 4A is a view showing consecutive images of 1 mM NaCl solution oscillating at 1 Hz in the T channel, according to the present invention.

To investigate the behavior of oscillating electroosmotic flow, consecutive images of the 1 mM NaCl solution oscillating at 1 Hz have been taken. The images are shown in FIG. 4A. The consecutive images in FIG. 4A show the maximum and minimum of the oscillating amplitude. The period between the maximum and the minimum oscillating amplitude is 0.5 sec which corresponds to the period of the externally applied electric field. This phenomenon can be explained by the small Reynolds number of the fluid flow in this experiment (Re<1). In this case, the inertia effect is negligible, therefore, the system is linear and the flow has the same period as the applied electric field.

Figure 4B:
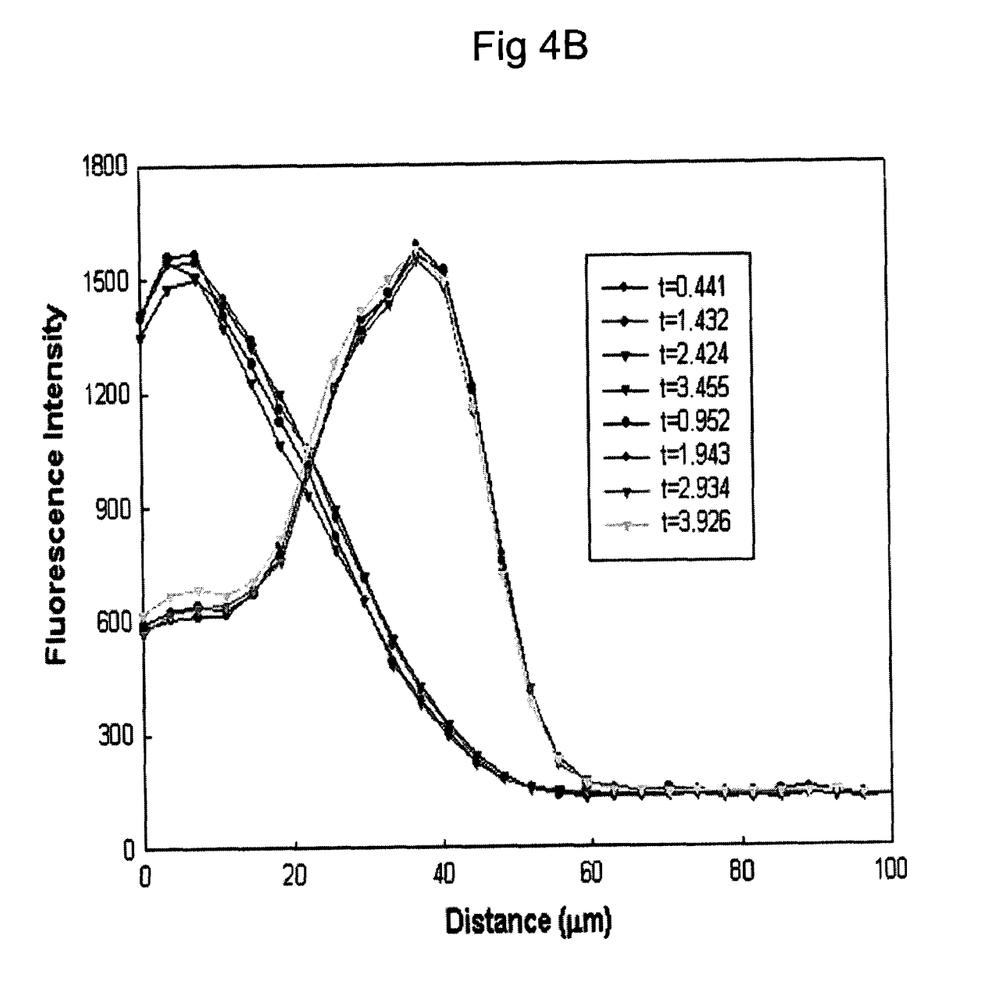
FIG. 4B is a plot of fluorescence intensity versus position of the 1 mM NaCl solution oscillating at 1 Hz in the T channel, according to the present invention.

Then, the oscillating behavior has been determined by measuring the time dependence of fluorescence intensity at specific positions from the inner wall of the T channel. The fluorescence intensity measured at particular positions at the left side within the T channel is as shown in FIG. 4A at the intervals where the amplitude reaches maximum and minimum values. The above measurement positions are located between a and b at the left side within the T channel as shown in FIG. 4A. The resultant fluorescence intensity profiles are shown in FIG. 4B. The intensity profile shows that the maximum and minimum values of the amplitude do not vary in time and the multiple intensity data for the maximum and minimum value of the amplitude can be obtained by one experiment. The position in the bottom of the FIG. 4B corresponds to a distance from the lowest position (a) in FIG. 4A.

The experiment was performed for the cases in a frequency range from 0.5 to 2 Hz. Although we have not quantitatively characterized the relationship between the oscillating amplitude and the zeta potential of NaCl solution, the feasibility of the present method is validated by these experiments.

It was impossible to obtain the apparent oscillating behavior for a frequency higher than 5 Hz. At this frequency, the oscillating behaviors look almost as that of a static electric field and the oscillating amplitude is too small to distinguish its maximum and minimum.

Therefore, we can conclude that there exists a suitable frequency range to observe the oscillating interface for a given electric field and T channel geometry. The frequency range must be specified before measuring the zeta potential using the present method.

As apparent from the above description, according to the present invention, a zeta potential of a wide range can be determined without using tracer particles and without contaminating the channel.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for determining a zeta potential generated between a channel wall and a fluid, the method comprising:
   (a) injecting an electrolyte solution into a first inlet of a T channel, which is provided with first and second inlet electrodes and a grounded outlet electrode, and a mixed solution of the electrolyte solution and a fluorescent dye into a second channel of the T channel and maintaining a steady-state of the two solutions;
   (b) applying a direct current electric field from the first and second electrodes to the outlet electrode to form an interface between the electrolyte solution and the mixed solution;
   (c) applying an alternating current electric field from one of the two inlet electrodes to the outlet electrode to oscillate the interface; and
   (d) measuring an amplitude of oscillation of the interface and determining the zeta potential from the standard relationship between the zeta potential and the amplitude.

2. The method according to claim 1, wherein the amplitude of oscillation of the interface is measured using a fluorescence microscope.

3. The method according to claim 1, wherein the direct current electric field is in the range of 100 to 2,000 V/cm.

4. The method according to claim 1, wherein the frequency of the alternating current electric field is in the range of 1 to 10 Hz.

* * * * *